United States Patent [19]

Liesse

[11] 4,167,223

[45] Sep. 11, 1979

[54] MECHANICALLY OPERABLE ACOUSTIC FILTER

[76] Inventor: Michel Liesse, La Bearnerie-Nesploy, 45270 Bellegarde, France

[21] Appl. No.: 916,840

[22] Filed: Jun. 19, 1978

[30] Foreign Application Priority Data

Jun. 27, 1977 [FR] France .............................. 77 19559

[51] Int. Cl.² .............................................. A61B 7/02
[52] U.S. Cl. .................................... 181/131; 179/180
[58] Field of Search ............... 181/157, 160, 131, 132, 181/137; 179/1 ST, 1 D, 107 FD, 180

[56] References Cited

U.S. PATENT DOCUMENTS

| 585,525 | 6/1897 | Kellogg | 181/131 |
| 1,429,664 | 9/1922 | Wood | 181/171 |
| 1,994,008 | 3/1935 | Torrance, Jr. | 181/131 |
| 2,792,902 | 5/1957 | Reichardt | 181/137 |
| 3,690,404 | 9/1972 | Collins | 181/131 |

*Primary Examiner*—Stephen J. Tomsky
*Attorney, Agent, or Firm*—Diller, Ramik & Wight

[57] ABSTRACT

A mechanically operable acoustic filter for varying the acoustic spectrum of transmitted sound signals. Sound signals, e.g. from a patient's skin when the filter is incorporated into the chest piece of a stethoscope, are received at an inlet orifice which may or may not be provided with an outer diaphragm. A thin, preferably Mylar filtering diaphragm partitions the interior of the chest piece into two chambers communicating with respective inlet and outlet orifices and each other through a central opening in the filtering diaphragm in line with a central passageway in a tensioning member for the filtering diaphragm. The position of the tensioning member is adjustable by a knob disposed outside the chest piece between a first position in which all frequencies pass by way of the central opening and successive positions in which the diaphragm is correspondingly tensioned at the same time the free vibrating area thereof is reduced.

10 Claims, 4 Drawing Figures

MECHANICALLY OPERABLE ACOUSTIC FILTER

BACKGROUND OF THE INVENTION

The present invention relates to mechanically operable acoustic filters for varying the acoustic spectrum of sound signals transmitted. Such a filter is adapted for use in acoustic devices or instruments, namely stethoscopes.

Among present-day acoustic filters two types may be discerned:

(1) filters utilizing electronic amplifiers in which the signals are modified and filtered, as desired, by electronic means and then reconverted into sound waves;

(2) other filters in which the sound waves cannot be filtered variably and continuously.

A stethoscope is known having two chest pieces one of which is an open, filterless chest piece and the other chest piece is fitted with a rigid diaphragm which is applied against the patient's skin in use. The amount of filtering produced by such a stethoscope is fixed and the filter member (i.e. the diaphragm) acts positively and directly on the sound source by its contact with the skin of the patient.

There are other known stethoscopes having a single chest piece which are provided with a diaphragm against which a smaller diameter annular member is applied to achieve two fixed filter settings and others with a diaphragm which, depending on the pressure with which its applied against the patient's skin modify the response curve of the transmitted sound waves.

Non-electrical devices are also known in which (1) the response curve is fixed; (2) if it is not fixed it is obtained by varying the pressure exerted on the skin which makes their use inconvenient and their results inaccurate; and (3) the variation of the response curve is effected by contact of the diaphragm with the patient's skin and not by acting directly on sound waves transmitted through a gaseous medium, which limits their use to medical stethoscopes.

SUMMARY OF THE INVENTION

An object of the present invention is the provision of an acoustic filter providing a continuous, variable mechanical modification of the response curve by acting on sound waves transmitted in a gaseous medium, which is accurate and independent of the sound source.

According to the invention there is provided a mechanically operable acoustic filter for varying the acoustic spectrum of sound signals transmitted, comprising a housing having an inlet orifice for receiving input sound signals and an outlet orifice for transmitting output sound signals, the orifices being disposed on opposite sides and spaced from a filtering diaphragm partitioning the interior of the housing into two chambers each in direct communication with one of the orifices. The acoustic filter is characterized by a tensioning member having adjustment means adapted to be adjusted from outside the housing for varying the pressure on the filtering diaphragm, the operative surface of the tensioning member being constructed and shaped so that the free vibrating surface of the diaphragm diminishes as the tension thereof increases.

As the filtering diaphragm is tensioned and its free surface area is reduced, the low frequencies are attenuated by the filter.

According to the preferred form of the filter the diaphragm is very thin and secured at its periphery to a rigid support, and the tensioning member has a wide convex operative surface adapted to bear at the middle of the filtering diaphragm.

The pressure exerted by the tensioning member on the filtering diaphragm is adjustable by the adjustment member.

When the pressure exerted on the diaphragm is minimal the contact area of the tensioning member on the filtering diaphragm is also at a minimum. In this position virtually the entire surface of the member is free and is adapted to be vibrated by the input sound waves; the filtering diaphragm then offers little resistance over the entire range of input sound frequencies.

As recited above, as the pressure exerted by the tensioning member increases, the filtering diaphragm is tensioned and the surface area in contact with the tensioning member expands since the filtering diaphragm mates with the convex operating surface of the tensioning member thereby diminishing its free vibrating surface correspondingly. These effects are complementary and the filter offers high resistance to low frequency sound waves and low resistance to high frequency sound waves.

These and other features and advantages of the invention will be brought out in the following description, given by way of example, with reference to the accompanying drawings.

DESCRIPTION OF A PREFERRED EMBODIMENT

Figure 1:
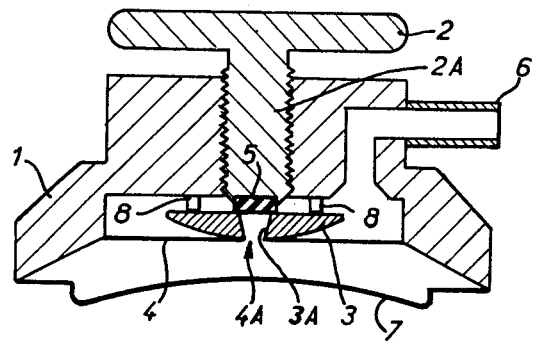
FIG. 1 is a schematic sectional view of a mechanical operable acoustic filter embodying the present invention.

According to a preferred embodiment, the mechanical operable acoustic filter, when part of a stethoscope, comprises a chest piece including a housing 1, an adjustment member 2 having a stem 2A, a convex disc-like tensioning member 3, a thin filtering diaphragm 4, a sealing member 5 fixed to the end of the stem 2A remote from the knob or member at the other end of the stem 2A and an outlet flexible tube 6 adapted to be connected to ear pieces (not shown) of the stethoscope as is conventional. The inlet orifice for receiving input sound waves from the patient may be open or fitted with another, outer diaphragm 7 as illustrated. The filtering diaphragm 4 formed, in practice, of glycolethylene terephtalate (Mylar) and 10 microns thick gives good results.

The stem 2A is advantageously threaded for upward and downward displacement in the housing 1 in response to rotation of the adjustment knob or member 2. In the illustrated embodiment the filtering diaphragm is apertured with a central opening 4A which is in alignment with a passageway 3A through the middle of the tensioning member 3. The edge of the central opening 4A of the diaphragm is fixed at the periphery of the passageway 3A, for example by an annular rivet (not shown) protruding partially into the passageway 3A, or other suitable means, e.g. an adhesive.

Figure 2:
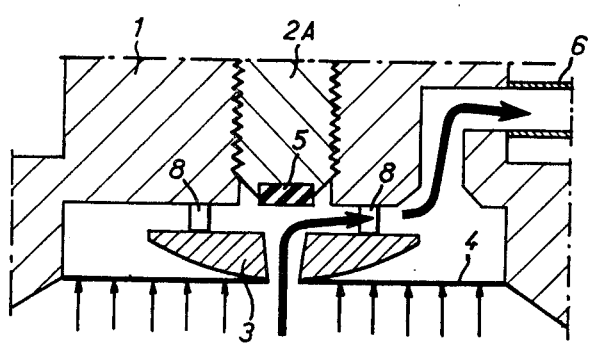
FIGS. 2–4 are schematic representations of the acoustic filter of FIG. 1 for different positions of the tensioning member.

When the adjustment knob or member 2 is completely unscrewed (FIG. 2) the sealing member is out of contact with the tensioning member 3. The tensioning member is held between the filtering diaphragm 4 at its connection with the tensioning member and suitably sized spacers 8. A ring (not shown) may be provided at the outer periphery of the filtering diaphragm 4 for setting the initial or rest position of the filter in order to compensate for manufacturing tolerances.

The sound waves of all the input frequencies pass directly by way of the central passageway 3A in the tensioning member 3 to the outlet orifice 6 and on to the ear pieces (not shown) of the stethoscope via flexible tubes.

Figure 3:
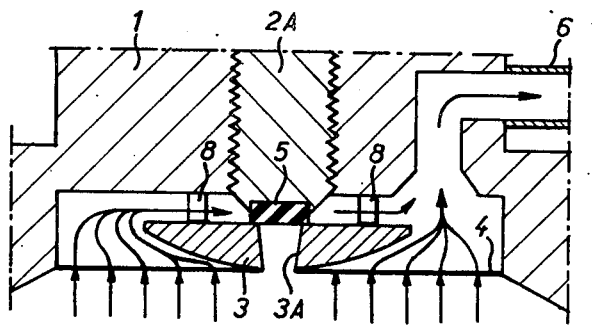

By screwing the adjustment knob or member 2 slightly downwards (FIG. 3) the sealing member comes into contact with the tensioning member 3 across the central passageway 3A and seals it off. Input sound waves must then pass through the thin filtering diaphragm 4. Since the thin diaphragm is only slightly tensioned and it is only slightly in contact with the tensioning member 3 the filter offers only slight resistance to low frequency sound signals and does not attenuate high frequencies.

Figure 4:
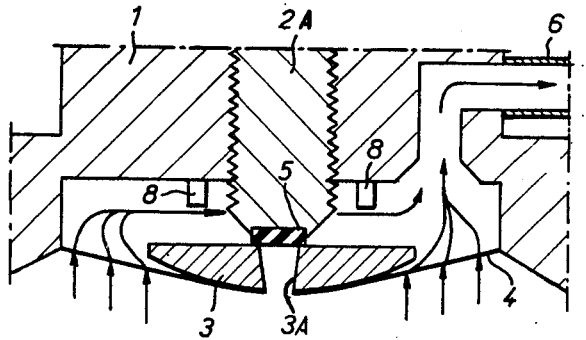

When the adjustment member 2 is screwed down further (FIG. 4) the central passageway 3A remains sealed off, the stem is moved downwards and displaces the tensioning member 3 therewith. The tensioning member 3 tensions the thin diaphragm 4 which mates with the convex operative surface thereof, increasing the contact surface area and diminishing the free vibrating surface of the diaphragm. The assembly then offers more resistance to low frequencies as the adjustment member is screwed down further.

The described and illustrated embodiment of the present selector is not intended to be restrictive. Rather, other applications, modifications and alternatives may be provided, within the scope of the appended claims.

According to an alternative embodiment, the tensioning member is made of deformable elastic material and bears either against the middle or the periphery of the filtering diaphragm. In accordance with the increase of pressure, the tension on the diaphragm increases as well as the contact area of the diaphragm with the operative surface of the tensioning member and therefore this embodiment produces substantially the same results as the aforesaid embodiment.

Instead of one tensioning member two such members may be arranged symmetrically one to each side of the filtering diaphragm, the contact surface increases symmetrical deformation of the two tensioning members but there is no tensioning of the filtering diaphragm. The effects develop in the same way as above but less quickly.

Furthermore, the invention is not limited to stethoscope but is applicable to head sets, loud speakers, noise-reducing earphones, sound pick-ups. The present invention may be oriented towards the atmosphere or in series in an acoustical conduit between a sound source and a sound pick-up, depending on whether high or low frequency sound waves are to attenuated for transmission to the pick-up.

What is claimed is:

1. A mechanically operable acoustic filter for varying the acoustic spectrum of sound signals transmitted therethrough, comprising a housing having an inlet orifice for receiving input sound signals and an outlet orifice for output sound signals, said orifices being disposed on opposite sides and spaced from a filtering diaphragm partitioning the interior of the housing into two chambers each in direct communication with a respective one of said orifices, the improvement comprising a tensioning member having an operative surface adapted to be brought into contact with said filtering diaphragm and in part setting-off a free vibrating surface area of said filtering diaphragm, adjustment means operative from outside said housing for varying the pressure exerted on said filtering diaphragm and progressively varying the tension of said free vibrating surface area, and the operative surface of said tensioning member being constructed and shaped so that the free vibrating surface area of said filtering diaphragm progressively diminishes or increases as the tension thereof increases or diminishes, respectively.

2. The acoustic filter according to claim 1, wherein said adjustment member includes a stem extending through a wall portion of said housing, said operative surface of said tensioning member being convex.

3. The acoustic filter according to claim 2, wherein said diaphragm is secured to said tensioning member.

4. The acoustic filter according to claim 3, further comprising a sealable opening through said diaphragm for permitting direct communication between said chambers.

5. The acoustic filter according to claim 4, wherein a passageway is defined in the middle of said tensioning member in alignment with a hole through the middle of the said diaphragm, said diaphragm being secured to said tensioning member at the periphery of said passageway.

6. The acoustic filter according to claim 5, wherein a sealing member for sealing off said passageway through said tensioning member is formed at the end of said stem facing said tensioning member.

7. The acoustic filter according to claim 1, further comprising spacer means for determining the maximum frequency spectrum position of said tensioning member when said adjustment means is out of contact with the latter, said spacer means being disposed on the side of the tensioning member remote from said operative surface of said tensioning member.

8. In a stethoscope, a chest piece for modifying the acoustic spectrum of sound signals transmitted therethrough to ear pieces of the stethoscope, comprising a housing having an inlet orifice adapted to the brought into position on the patient's skin and an outlet orifice adapted to be connected through a flexible tube to the ear pieces of the stethoscope, said orifices being disposed on opposite sides and spaced from a filtering diaphragm partitioning the interior of said housing into two chambers each in direct communication with a said orifice, a tensioning member having adjustment means operative from outside said housing for varying the pressure exerted on said diaphragm, the operative surface of said tensioning member being constructed and shaped so that the free vibrating surface of said diaphragm diminishes as the tension of said diaphragm increases.

9. A chest piece according to claim 8, further comprising an outer diaphragm adapted to be received at the inlet orifice of said housing and thereby closing the associated chamber on the side of said diaphragm remote from said tensioning member.

10. A chest piece according to claim 8 or 9, wherein said inlet orifice of said housing is sized and shaped so that when said chest piece is applied against a patient's skin said filtering diaphragm remains out of contact with the same.

* * * * *